United States Patent [19]
Pennig

[11] Patent Number: 5,376,090
[45] Date of Patent: Dec. 27, 1994

[54] CLAMPING COUPLING

[75] Inventor: Dietmar Pennig, Münster, Germany

[73] Assignee: Orthofix S.r.l., Bussolengo, Italy

[21] Appl. No.: 151,531

[22] Filed: Nov. 12, 1993

Related U.S. Application Data

[63] Continuation of Ser. No. 908,966, Jul. 6, 1992, abandoned.

[30] Foreign Application Priority Data

Jul. 12, 1991 [DE]  Germany .................. 9108566[U]

[51] Int. Cl.$^5$ ............................................. A61B 17/60
[52] U.S. Cl. .................................. 606/54; 606/59; 606/57; 403/59
[58] Field of Search .................. 403/53, 59, 60; 606/53–59

[56] References Cited

U.S. PATENT DOCUMENTS

| Re. 31,809 | 1/1985 | Danieletto et al. ............... 606/57 |
| 4,312,336 | 1/1982 | Danieletto et al. ............... 606/57 |
| 4,621,627 | 11/1986 | De Bastiani et al. .............. 606/57 |
| 4,714,076 | 12/1987 | Comte et al. ..................... 606/57 |
| 5,019,077 | 5/1991 | De Bastiani et al. .............. 606/54 |
| 5,026,372 | 6/1991 | Sturtzkopf et al. ................ 606/54 |
| 5,087,258 | 2/1992 | Schewior .......................... 606/56 |
| 5,152,280 | 10/1992 | Danieli ............................. 606/54 |

FOREIGN PATENT DOCUMENTS

| 8802463 | 5/1990 | Netherlands ...................... 606/54 |
| 9011727 | 10/1990 | WIPO ............................. 606/54 |
| 9111151 | 8/1991 | WIPO ............................. 606/54 |

Primary Examiner—Robert A. Hafer
Assistant Examiner—Brian E. Hanlon
Attorney, Agent, or Firm—Hopgood, Calimafde, Kalil & Judlowe

[57] ABSTRACT

A clamping coupling for fixing bone screws, pins or the like incorporates a rotary joint between the bone-screw fixing region of the coupling and a ball-joint connection region of the coupling, whereby an extended range of angular adaptability and fixation are achievable, as compared to the more limited range of angular articulation achieved by the ball-joint action alone.

1 Claim, 1 Drawing Sheet

CLAMPING COUPLING

This is a continuation of copending application Ser. No. 07/908,966, filed Jul. 6, 1992, abandoned.

BACKGROUND OF THE INVENTION

The invention relates to orthopedic-fixation devices and in particular to a clamping coupling for a fixator of the nature disclosed in U.S. Pat. No. 4,312,339 (now Reissue Patent No. Re. 31,809).

Said patent discloses an external fixator having a central body part with clamping means at each of the respective ends of the body part. Each of the clamping means is developed (1) to receive and fix in place bone screws or pins and (2) to detachably achieve a ball-joint connection to the central body part, via a bayonet lock or via a threaded lock. In this way, the bone screws are connected to the central body part of the fixator. The ball-joint connections arranged at the ends can be angularly adjusted to an angle of about 40°–45° with respect to the axis of the central part of the fixator, which is insufficient in certain cases.

BRIEF STATEMENT OF THE INVENTION

The object of the present invention is to improve this indicated type of clamping coupling in such a way, that, without great expense, larger angles can be achieved between the central part of the fixator and the clamping coupling itself.

This object, which forms the basis of the invention, is achieved by providing a clamping coupling wherein a rotary joint is interposed between the ball-joint connection and the half shell which bears the ball-joint connection proper.

By this arrangement, an angling by more than 90° is now made possible, all desired alignments being possible by the interposition of the ball point between the fastening cuff of the bayonet lock and the half shell.

DETAILED DESCRIPTION

Figure 1:
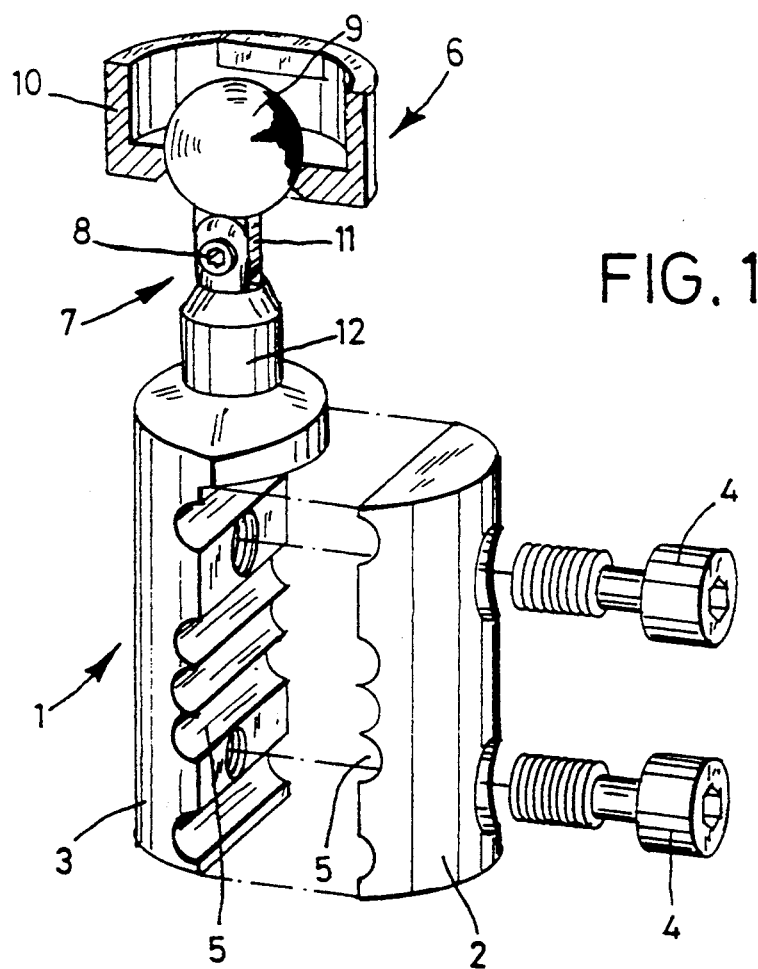
Figure 2:
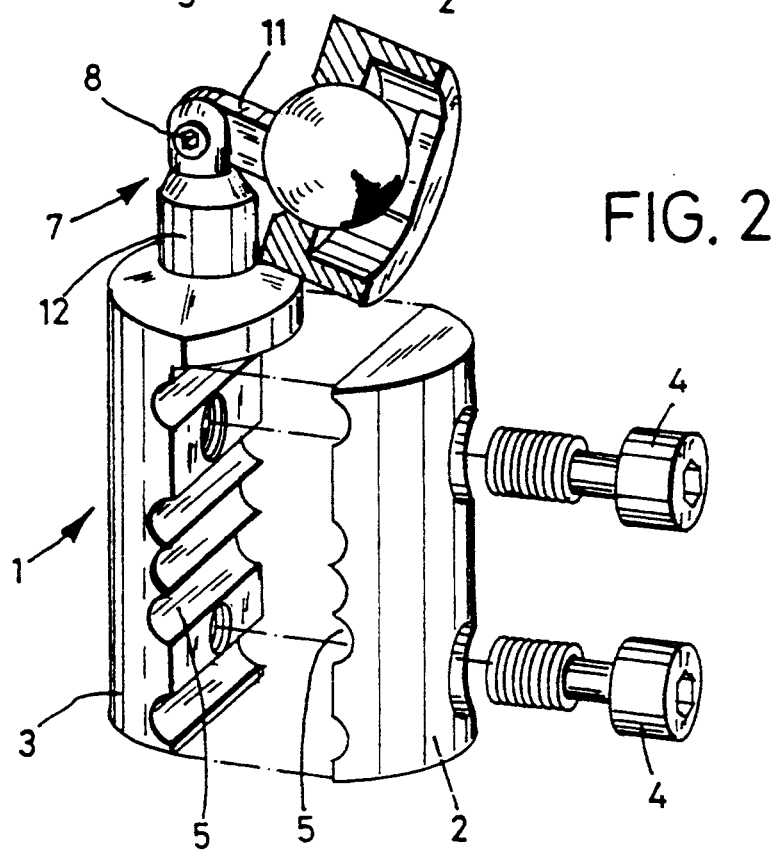

One embodiment of the invention will be explained below with reference to the accompanying drawings, in which:

FIG. 1 is an exploded view in perspective, partly in longitudinal section, showing a clamping coupling of the invention; and FIG. 2 is a similar view to illustrate enhanced angling through use of the coupling of FIG. 1.

The drawing shows a clamping coupling 1 consisting essentially of two half shells 2 and 3, which can be fastened to each other by screws 4. Within the half shells 2 and 3 there are recesses 5 which will be understood to serve to receive and fix bone pins, screws or the like. The half shell 3 carries, as a rigid attachment, a ball-joint connection 6 for a bayonet lock or screw lock by which the clamping coupling 1 can be connected to an outer end of a known external fixator. The ball joint connection 6 consists of a ball 9 and a ring 10 which serves for detachable connection to the fixator.

In the prior art, the ball 9 of the ball-joint connection 6 directly and rigidly adjoins the half shell 3, but according to the invention, a rotary joint 7 is interposed between these two parts 3 and 6. The rotary joint 7 has a pivot pin 8, which will be understood to include threads by which the angle of the rotary joint 7 can be clamped or fixed, as by wrench application. The ball 9 adjoins the pivot pin 8 via a shank portion 11, and the half shell 3 adjoins pin 8 via a collar or shank portion 12. By this arrangement it is possible to swing the actual ball-joint connection 6 by, for instance, 90° with respect to the clamping shell 3 and to fix it in position, so that the range of use of the clamping coupling is thereby increased.

Furthermore, the ring 10 can, of course, be swivelled on the ball 9, as in the prior art.

What is claimed is:

1. As an article of manufacture, a clamping coupling comprising two elongate half shells having confronting separable portions that are grooved for reception of bone screws or bone pins, clamp bolts for clamping said half shells together for fixed retention of bone screws or bone pins in said grooves, a first shank portion extending longitudinally beyond a longitudinal end of one of said half shells, ball-joint connecting means and a second shank portion extending longitudinaly from said ball-join means, said shank portions being of substantially equal effective length, and a selectively clampable hinge connecting said first and second shank portions.

* * * * *